(12) United States Patent
Buschle et al.

(10) Patent No.: US 8,277,815 B2
(45) Date of Patent: *Oct. 2, 2012

(54) PHARMACEUTICAL COMPOSITION COMPRISING AN ANTIGEN

(75) Inventors: Michael Buschle, La Chaux-de-Fonds (CH); Julia-Kristina Fleitmann, Gallbrunn (AT); Frank Mattner, Vienna (AT); Jack Melling, Stroudsburg, PA (US)

(73) Assignee: Intercell AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/110,454

(22) Filed: May 18, 2011

(65) Prior Publication Data

US 2011/0300169 A1 Dec. 8, 2011

Related U.S. Application Data

(63) Continuation of application No. 12/248,397, filed on Oct. 9, 2008, now abandoned, which is a continuation of application No. 11/082,595, filed on Mar. 17, 2005, now abandoned, which is a continuation of application No. 10/114,823, filed on Apr. 1, 2002, now abandoned, which is a continuation of application No. PCT/EP00/09657, filed on Oct. 2, 2000.

(30) Foreign Application Priority Data

Oct. 1, 1999 (AT) ......................................... 1680/99

(51) Int. Cl.
*A61K 38/00* (2006.01)
*A61K 39/12* (2006.01)
*A61K 45/00* (2006.01)

(52) U.S. Cl. ............... 424/186.1; 424/189.1; 424/278.1; 530/300

(58) Field of Classification Search ........................ None
See application file for complete search history.

(56) References Cited

U.S. PATENT DOCUMENTS

| | | | |
|---|---|---|---|
| 3,725,545 A | 4/1973 | Maes | |
| 4,777,245 A | 10/1988 | Foung et al. | |
| 5,252,327 A | 10/1993 | Bernhardt | |
| 5,562,910 A | 10/1996 | Daynes et al. | |
| 5,980,911 A | 11/1999 | Corner et al. | |
| 6,172,189 B1 | 1/2001 | Devare et al. | |
| 6,231,859 B1 | 5/2001 | Kensil | |
| 6,558,670 B1 | 5/2003 | Friede et al. | |
| 6,572,866 B1 | 6/2003 | Torcia | |
| 6,593,296 B1 * | 7/2003 | Charman et al. | 514/11.3 |
| 7,001,890 B1 | 2/2006 | Wagner et al. | |
| 2003/0099663 A1 | 5/2003 | Fleitmann et al. | |
| 2003/0152580 A1 | 8/2003 | Sette et al. | |
| 2005/0163797 A1 | 7/2005 | Fleitmann et al. | |
| 2009/0060875 A1 * | 3/2009 | Frisch et al. | 424/85.7 |
| 2009/0104217 A1 | 4/2009 | Fleitmann et al. | |

FOREIGN PATENT DOCUMENTS

| | | |
|---|---|---|
| AU | 199718759 B2 | 9/1997 |
| EP | 0 445 020 A1 | 9/1991 |
| EP | 1 195 381 A1 | 4/2002 |
| GB | 1290141 A | 9/1972 |
| WO | WO-91/04052 A1 | 4/1991 |
| WO | WO-91/16921 A1 | 11/1991 |
| WO | WO-92/17493 A2 | 10/1992 |
| WO | WO-94/15634 A1 | 7/1994 |
| WO | WO-95/05195 A1 | 2/1995 |
| WO | WO-95/12677 A2 | 5/1995 |
| WO | WO-95/27733 A1 | 10/1995 |
| WO | WO-97/30721 A1 | 8/1997 |
| WO | WO-98/32456 A1 | 7/1998 |
| WO | WO-99/02183 A2 | 1/1999 |
| WO | WO-99/27959 A1 | 6/1999 |
| WO | WO-99/28759 A1 | 6/1999 |
| WO | WO-00/11186 A1 | 3/2000 |
| WO | WO-01/21189 A1 | 3/2001 |
| WO | WO-2005/004910 A2 | 1/2005 |

OTHER PUBLICATIONS

U.S. Appl. No. 60/745,548, filed Apr. 25, 2006, von Gabain.
Alexander et al., Recognition of a novel naturally processed, A2 restricted, HCV-NS4 epitope triggers IFN-gamma release in absence of detectable cytopathicity. Hum Immunol. Dec. 1998;59(12):776-82.
Armstrong et al., Neuropeptides in the skin: interactions between the neuroendocrine and the skin immune systems, Exp. Dermatol., 7:81-96, 1998.
Aronin et al., Substance P and Neurotensin: their roles in the regulation of anterior pituitary function, Ann. Rev. Physiol., 48:537-549, 1986.
Azuma, Synthetic immunoadjuvants: application to non-specific host stimulation and potentiation of vaccine immunogenicity. Vaccine. 1992;10(14):1000-6.
Battegay et al., Patients with chronic hepatitis C have cirsulating cytotoxic T cells which recignize hepatitis C virus-encoded peptides binding to HLA-A2.1 molecules, J. of Virology, 69(4):2462-2470, 1995.
Bellentani et al., Epidemiology of hepatitis C virus infection in Italy: the slowly unraveling mystery. Microbes Infect. Nov. 2000;2(14):1757-63.

(Continued)

*Primary Examiner* — Zachariah Lucas
*Assistant Examiner* — Michelle S Horning
(74) *Attorney, Agent, or Firm* — Wolf, Greenfield & Sacks, P.C.

(57) ABSTRACT

The invention relates to immunogenic compositions. In certain embodiments, the invention provides pharmaceutical compositions comprising an antigen, an immunostimulating substance selected form neuroactive compounds, hormones, compounds having a growth hormone activity, and mixtures thereof, and a polycationic polymer.

14 Claims, 2 Drawing Sheets

OTHER PUBLICATIONS

Berczi, Pituitary hormones and immune function. Acta Paediatr Suppl. Nov. 1997;423:70-5.

Bold et al., Nerve growth factor as a mitogen for a pancreatic carcinoid cell line, J. of Neurochemistry, 64:2622-2628, 1995.

Buschle et al., Chemically defined, cell-free cancer vaccines: use of tumor antigen-derived peptides of polyepitope proteins for vaccination, Gene Ther. Mol. Biol., 1:309-321, 1998.

Buschle et al., Transloading of tumor antigen-derived peptides into antigen-presenting cells, Proceeding of the National Academy of Sciences, USA, 94 (7): 3256-3261, 1997.

Buts, Bioactive factors in milk, Archives de Pediatrie, 5:298-306, 1998, NCBI English abstract.

Cerny et al., Cytotoxic T lymphocyte response to hepatitis C virus-derived peptides containing the HLA A2.1 binding motif, J. of Clinical Investigation, 95 (2): 521-530, 1995.

Chappel, Growth hormone in immune reconstitution, J. Acquired Immune Deficiency Syndromes and Human Retrovirology, 20:423-431, 1999.

Cornberg et al., Treatment of chronic hepatitis C with PEGylated interferon and ribavirin, Current Gastroenterology Reports, 4:23-30, 2002.

Downing and Miyan, Neural immunoregulation: emerging roles for nerves in immune homeostasis and disease, Immunol. Today, 21(6):281-289, 2000.

Duenas-Carrera, Biotechnology & Applied Biochemistry, manuscript BA20030112, published Sep. 29, 2003.

Firbas et al., Immunogenicity and safety of a novel therapeutic hepatitis C virus (HCV) peptide vaccine: A randomized, placebo controlled trial for dose optimization in 128 healthy subjects, Vaccine, 24:4343-4353, 2006.

Goldman and Bar-Shavit, On the mechanism of the augmentation of the phagocytic cells by tuftsin, substance P, neurotensin, and kentsin and the interrelationship between their receptors, Annals New York Academy of Science, 419:143-155, 1983.

Heile et al., Evaluation of hepatitis C virus glycoprotein E2 for vaccine design: an endoplasmic reticulum-retained recombinant protein is superior to secreted recombinant protein and DNA-based vaccine candidates, J of Virology, 74:6885-6892, 2000.

Hoffmann et al., Mapping of immunodominant CD4+ T lymphocyte epitopes of hepatitis C virus antigens and their relevance during the course of chronic infection. Hepatology. Mar. 1995;21(3):632-8.

Koziel et al., Hepatitis C virus (HCV)-specific cytotoxic T lymphocytes recognize epitopes in the core and envelope proteins of HCV. J Virol. Dec. 1993;67(12):7522-32.

Koziel et al., HLA class I-restricted cytotoxic T lymphocytes specific for hepatitis C virus. Identification of multiple epitopes and characterization of patterns of cytokine release. J Clin Invest. Nov. 1995;96(5):2311-21.

LaMonaca et al., Conserved hepatitis C virus sequences are highly immunogenic for CD4(+) T cells: implications for vaccine development. Hepatology. Oct. 1999;30(4):1088-98.

Lauer et al., Vaccine-induced T-cell responses against HCV: one step taken, more to follow. Gastroenterology. Apr. 2007;132(4):1626-8.

Lechmann et al., T- and B-cell responses to different hepatitis C virus antigens in patients with chronic hepatitis C infection and in healthy anti-hepatitis C virus—positive blood donors without viremia. Hepatology. Oct. 1996;24(4):790-5.

Levite, Neuropeptides, by direct interactions with T cells, induce cytokine secretion and break the commitment to a distinct T helper phenotype, Proc. Natl. Acad. Sci. USA, 95:12544-12549, 1998.

Liang et al., Pathogenesis, natural history, treatment, and prevention of hepatitis C, Annals of Internal Medicine, 132:296-305, 2000.

Magklara et al., Human glandular kallikrein in breast milk, amniotic fluid, and breast cyst fluid, Clinical Chemistry, 45:1774-1780, 1999.

Manns et al., The way forward in HCV treatment—finding the right path. Nat Rev Drug Discov. Dec. 2007;6(12):991-1000.

Mellado et al., HIV-1 envelope protein gp120 triggers a Th2 response in mice that shifts to Th1 in the presence of human growth hormone, Vaccine, 16(11/12):1111-1115, 1998.

Neely and Rosenfeld, Use and abuse of human growth hormone, Annu. Rev. Med., 45:407-420, 1994.

Office Action, mail date Apr. 9, 2008.
Office Action, mail date Dec. 15, 2004.
Office Action, mail date Dec. 21, 2006.
Office Action, mail date Dec. 31, 2003.
Office Action, mail date Feb. 7, 2006.
Office Action, mail date Jan. 11, 2005.
Office Action, mail date Jun. 2, 2004.
Office Action, mail date May 25, 2007.
Office Action, mail date May 31, 2006.

Rehermann et al., Differential cytotoxic T-lymphocyte reponsiveness to the hepitis B and C viruses in chronically infected patients, J. of Virology 70(10): 7092-7102, 1996.

Rollier et al., Control of heterologous hepatitis C virus infection in chimpanzees is associated with the quality of vaccine-induced peripheral T-helper immune response, J of Virology, 78:187-196, 2004.

Sarobe et al., Enhanced in vitro potency and in vivo immunogenicity of a CTL epitope from hepatitis C virus core protein following amino acid replacement at secondary HLA-A2.1 binding positions. J Clin Invest. Sep. 15, 1998;102(6):1239-48.

Schlaphoff et al., Functional and phenotypic characterization of peptide-vaccine-induced HCV-specific CD8+ T cells in healthy individuals and chronic hepatitis C patients. Vaccine. Sep. 17, 2007;25(37-38):6793-806. Epub Jun. 29, 2007.

Schmidt et al., Cell-free tumor antigen peptide-based cancer vaccines. Proc Natl Acad Sci U S A. Apr. 1, 1997;94(7):3262-7.

Scognamiglio et al., Presence of effector CD8+ T cells in hepatitis C virus-exposed healthy seronegative donors. J Immunol. Jun. 1, 1999;162(11):6681-9.

Shirai et al., An epitope in hepatitis C virus core region recognized by cytotoxic T cells in mice and humans. J Virol. May 1994;68(5):3334-42.

Singh and O'Hagan, Advances in vaccine adjuvants, Nature Biotechnology, 17(11):1075-1081, 1999.

Spriggs, Shared resources between the neural and immune systems: semaphorins join the ranks, Curr. Opinion Immunology, 11:387-391, 1999.

Stephenson et al., Adjuvant effect of human growth hormone with an inactivated flavivirus vaccine, J. Infectious Diseases, 164:188-191, 1991.

Wong et al., Induction of primary, human antigen-specific cytotoxic T lymphocytes in vitro using dendritic cells pulsed with peptides. J Immunother. Jan. 1998;21(1):32-40.

Wong et al., Liver-derived CTL in hepatitis C virus infection: breadth and specificity of responses in a cohort of persons with chronic infection, J. of Immunology, 160 (3): 1479-1488, 1998.

* cited by examiner

SEQUENCE LISTING

```
<160> NUMBER OF SEQ ID NOS: 24

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Lys Phe Pro Gly Gly Gly Gln Ile Val Gly Gly Val Tyr Leu Leu Pro
 1               5                  10                  15

Arg Arg Gly Pro Arg Leu
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Ala Asp Leu Met Gly Tyr Ile Pro Leu Val Gly Ala Pro Leu Gly Gly
 1               5                  10                  15

Ala Ala Arg Ala
            20

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Asp Leu Met Gly Tyr Ile Pro Ala Val
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Cys Ile Asn Gly Val Cys Trp Thr Val
 1               5

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Ser Pro Val Phe Thr Asp Asn Ser Ser Pro Pro Ala Val Pro Gln Ser
 1               5                  10                  15
```

-continued

Phe Gln Val Ala
            20

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Gly Tyr Lys Val Leu Val Leu Asn Pro Ser Val Ala Ala Thr
1               5                   10

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Tyr Leu Val Ala Tyr Gln Ala Thr Val Cys Ala Arg Ala Gln Ala Pro
1               5                   10                  15

Pro Pro Ser Trp
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Val Val Thr Ser Thr Trp Val Leu Val Gly Gly Val Leu Ala Ala Leu
1               5                   10                  15

Ala Ala Tyr Cys Leu
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Met Trp Asn Phe Ile Ser Gly Ile Gln Tyr Leu Ala Gly Leu Ser Thr
1               5                   10                  15

Leu Pro Gly Asn
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Gly Glu Gly Ala Val Gln Trp Met Asn Arg Leu Ile Ala Phe Ala Ser

```
                 1               5                  10                 15
Arg Gly Asn His Val
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Pro Ala Ile Ala Ser Leu Met Ala Phe Thr Ala Ala Val Thr Ser Pro
  1               5                  10                 15

Leu Thr Thr Gly
            20

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Ile Ala Ser Leu Met Ala Phe Thr Ala Ala Val Thr Ser
  1               5                  10

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 13

Gln Thr Leu Leu Phe Asn Ile Leu Gly Gly Trp Val Ala Ala Gln Leu
  1               5                  10                 15

Ala Ala Pro Gly
            20

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

Phe Asn Ile Leu Gly Gly Trp Val Ala Ala Gln Leu Ala
  1               5                  10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 15

Val Tyr Asp Phe Phe Val Trp Leu
  1               5
```

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ser Ile Ile Asn Phe Glu Lys Leu
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Phe Leu Leu Leu Ala Asp Ala Arg Val
 1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Val Gly Gly Val Tyr Leu Leu Pro Arg Arg
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Tyr Leu Leu Pro Arg Arg Gly Pro Arg Leu
 1               5                  10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Asp Leu Met Gly Tyr Ile Pro Leu Val
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide 
```
<400> SEQUENCE: 21

Ser Leu Tyr Asn Thr Val Ala Thr Leu
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 22

Asp Pro Asn Pro Gln Glu Val Val Leu
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 23

Ile Leu Lys Glu Pro Val His Gly Val
 1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 24

Arg Pro Lys Pro Gln Gln Phe Phe Gly Leu Met
 1               5                  10
```

PHARMACEUTICAL COMPOSITION COMPRISING AN ANTIGEN

CROSS-REFERENCE TO RELATED APPLICATIONS

This application is a continuation of U.S. application Ser. No. 12/248,397 filed 9 Oct., 2008, now abandoned, which is a continuation of U.S application Ser. No. 11/082,595 filed 17 Mar. 2005, now abandoned, which is a continuation of U.S. application Ser. No. 10/114,823 filed on 1 Apr. 2002, now abandoned, which is a continuation of PCT Application No. PCT/EP00/09657 filed 2 Oct. 2000, which claims priority to Austrian Application No. A 1680/99 filed 1 Oct. 1999. The entire text of each of the above-referenced disclosures is specifically incorporated by reference herein.

BACKGROUND

The invention relates to a pharmaceutical composition especially to be used as a vaccine.

Vaccines are a very successful, yet cost saving medical intervention. Several catastrophic illnesses including small pox and poliomyelitis have been, due to intense vaccination programmes, eliminated from the face of this earth or are on the brink of extinction (Nossal, Nat Med 4, (1998), 475-476). In fact, vaccines can save more lives (and money) than any other medical intervention. Although this notion is valid for a whole panel of diseases including tuberculosis, diphteria, pertussis, measles and tetanus, there are no effective vaccines for numerous ailments including most viral infections, such as AIDS, and other illnesses including malaria, or even cancer. In addition, the rapid emergence of antibiotic resistant bacteria and microorganisms calls for alternative treatments with vaccines being a logical choice. Finally, the great need for vaccines is also illustrated by the fact that infectious diseases, rather than cardiovascular disorders or cancer or injuries remain the largest cause of death and disability in the world (Bloom et al, Nat Med 4, (1998), 480-484).

The main problem in the field of vaccines is that traditional vaccines (and/or the immune modulating compounds contained within these preparations) are designed to induce high levels of antibodies (Harlow et al, Cold Spring Harbor: Cold Spring Harbor Laboratory, (1988)). Unfortunately, antibodies on their own are not effective in preventing many diseases including most illnesses caused by viruses, intracellular bacteria, or certain parasites. Examples are pathogens such as the above-mentioned HIV virus or Plasmodium spec. in case of malaria. In addition, these vaccines likely will not be effective in cancer. In numerous experimental systems it has been shown that the cellular arm of the immune system, including T cells, rather than the humoral arm, is important for these indications. Therefore, novel, innovative technologies to overcome the limitations of conventional vaccines are needed. The focus must be on technologies that reliably induce the cellular immune system, including antigen specific T cells, which recognize molecules expressed on pathogen infected cells. Ideally, vaccines are designed that induce both T cells distinguishing diseased, and/or infected cells from normal cells and, simultaneously, antibodies secreted by B cells recognizing pathogens in extracellular compartments.

Commonly, vaccines are administered as a combination of pathogen-derived antigens together with compounds that induce or enhance immune responses against these antigens (these compounds are usually termed adjuvants). Examples of antigens are whole organisms such as inactivated or attenuated viruses or bacteria, fungi, protozoa or even cancer cells. Antigens may also consist of subfractions of theses organism/tissues, proteins or, in their most simple form, peptides. Antigens can also be recognized by the immune system in form of glycosylated proteins or peptides and may also be or contain polysaccharides or lipids. Short peptides can be used since for example cytotoxic T cells recognize antigens in form of short usually 8-11 amino acids long peptides in conjunction with major histocompatibility complex (MHC) (Rammensee et al., Immunogenetics 41, (1995), 178-228). B cells recognize longer peptides starting at around 15 amino acids (Harlow et al, Cold Spring Harbor: Cold Spring Harbor Laboratory, (1988)). By contrast to T cell epitopes the three dimensional structure of B cell antigens may also be important for recognition by antibodies. In order to obtain sustained, antigen-specific immune responses, adjuvants need to trigger immune cascades that involve all cells of the immune system necessary. Primarily, said adjuvants are acting, but are not restricted in their mode of action, on so-called antigen presenting cells (APCs). These cells usually first encounter the antigen(s) followed by presentation of processed or unmodified antigen to immune effector cells. Intermediate cell types may also be involved. Only effector cells with the appropriate specificity are activated in a productive immune response. The adjuvant may also locally retain antigens and co-injected other factors. In addition the adjuvant may act as a chemoattractant for other immune cells or may act locally and/or systemically as a stimulating agent for the immune system.

Human growth hormone (HGH) is a pituitary-derived factor primarily described for its ability to promote growth acceleration (reviewed in Neely et al, Annu Rev Med 45, (1994), 407-420). The first patient was treated with growth hormone obtained from pituitary extracts as early as 1958. Recombinant HGH is available for roughly 15 years now and has been used extensively in the clinic. Side effects of recombinant HGH are rare. Efficacy of recombinant HGH preparations has been demonstrated in a wide spectrum of diseases including Turner syndrome, idiopathic short stature, growth hormone deficiency and renal failure.

Whilst numerous studies have confirmed the growth promoting effect of HGH, relatively few reports address a possible interaction of this molecule with cells of the immune system. Stephenson and Melling, who showed that HGH greatly enhances the efficacy of a viral vaccine preparation, first demonstrated the usefulness of HGH in a vaccine context (Stephenson et al., J Infect Dis 164, (1991), 188-191). They co-injected HGH with a vaccine for tick-born encephalitis (TBE) virus, an endemic virus transmitted by ticks. In animal experiments HGH potentiated vaccine efficacy and led to the protection of animals after only one injection of the vaccine. The mechanism of how HGH enhanced vaccine efficacy is unclear, but it was speculated that cell mediated immunity played a significant role. There is further, albeit circumstantial, evidence that HGH may indeed induce cellular immune reactions: Mellado et al. demonstrated that if an antigen derived from human immuno deficiency virus (HIV) is applied to mice, they develop a so called Thl type T helper cell response indicative of a cellular immune response (Mellado et al., Vaccine 16, (1998), 1111-1115). Taken together, there is circumstantial evidence that HGH, which is viewed as exemplary for a whole class of primarily neuroactive compounds (see e.g. Levite, PNAS 95 (1998), 12544-12549, Scholzen et al, Exp. Dermetal. 7 (1998), 81-96), may have a positive effect on the immune system, but the mechanisms remain unclear.

Polycationic polymers, for example the polycationic amino acid polymers poly-L-arginine and poly-L-lysine, have been shown to allow very efficient charging of antigen presenting cells (APCs) with antigens in vitro and in vivo (Buschle et al., Gene Ther Mol Biol 1, (1998), 309-321; Buschle et al., Proc Natl Acad Sci USA 94, (1997), 3256-3261; Schmidt et al., Proc Natl Acad Sci USA 94, (1997), 3262-3267). This is thought to be the key event for triggering immune cascades eventually leading to the induction of antigen specific immune effector cells that are able to destroy or neutralize targets. It has been shown previously that a number of polycationic compounds exert effects on immune cells (Buschle et al., Gene Ther Mol Biol 1, (1998), 309-321; Buschle et al., Proc Natl Acad Sci USA 94, (1997), 3256-3261).

Co-injection of a mixture of poly-L-arginine or poly-L-lysine together with an appropriate antigen as a vaccine protect animals from tumor growth in several animal models (Buschle et al., Gene Ther Mol Biol 1, (1998), 309-321; Schmidt et al., Proc Natl Acad Sci USA 94, (1997), 3262-3267). Thus, a vaccine consisting of polycationic compounds and antigen(s) is accepted in the art as being a very effective form of treatment.

GB 1 290 141 discloses a vaccine containing antigenic material with a base-rich peptide as an adjuvant. According to this document the vaccine may consist (as antigenic material) of live or killed organisms, whole or disrupted, or of preparations of natural toxins or products of the organism, or of preparations of extracts of the organisms, alone or in combination with one another. The base-rich peptide used as an adjuvant must contain at least 50% residues which have a free amino group, such as polylysine, polyornithine, polyarginine and polydiaminobutyric acids. In WO 97/30721 the use of basic polyamino acid as preferred adjuvant for vaccines in combination with an immunomodulating peptide or protein (fragment) is described. The use of a further immunostimulating substance to be used together with an antigen and such a polycationic polymer is neither disclosed nor made obvious by these two documents.

U.S. Pat. No. 3,725,545 describes that it is possible to potentiate the antibody production ability of nucleic acids containing preparations by adding cationically charged polymers in combination with single-stranded or multi-stranded nucleic acid polymers. Examples of such polycationic polymers are polyornithine, lysozyme, DEAE-Dextran, histone, hexadimethrine bromide and polylysine.

WO 91/04052 also relates to DEAE-Dextran as a polycationic adjuvant in a vaccine composition. This polycationic adjuvant is incorporated into a vaccine which further comprises the antigenic substance (the antigen) and saponin as a further adjuvant. Of course, neither polycationic compounds nor saponin as combined adjuvants may be regarded as an immunostimulating substance within the course of the present invention.

SUMMARY OF THE INVENTION

It is the object of the present invention to provide a pharmaceutical composition which allows an effective delivery to a target cell especially to the cellular immune system.

This object is solved by a pharmaceutical composition comprising
  an antigen,
  an immunostimulating substance selected from neuroactive compounds, hormones, compounds having a growth hormone activity and mixtures thereof, and
  a polycationic polymer.

It has surprisingly turned out that the combination of the selected immunostimulating substance according to the present invention and the polycationic polymer with an antigen leads to a synergistic immunomodulating effect for a given antigen preparation. Indeed, it turned out that the effect of an immunostimulating substance selected according to the present invention alone with the antigen has—for itself—even a lower effect than administering the antigen with the polycationic polymer alone.

The immunostimulating effect of substances such as human growth hormone (HGH) has been reported (see also: EP 0 434 749 B1, U.S. Pat. Nos. 4,837,202, 5,830,877 and 5,583,109). Indeed, many of the neuroactive substances, such as pituitary growth hormones also exhibit T cell inducing activity or cytokine secretion altering activities. These compounds also may act on APCs.

The immunostimulating effect is especially given as these substances e.g. induce T cells, B cells, NK cells or APCs or alter the cytokine secretion of T cells, B cells, NK cells or APCs.

It turned out, however, that administration of an antigen together with such immunostimulating substances alone does not lead to an efficient cellular immune response although such substances may have—as stated above—T cell inducing activity, are able to alter the cytokine secretion of T cells (s. Levite (1998), and Scholzen et al (1998)) or activate the immune system in a more general way.

The present invention is based on the careful selection of immunostimulating substances to be used in connection with the polycationic polymer. The polycationic polymer serves as adjuvant in the present invention. It is therefore clear that other adjuvants described in the prior art may not be regarded as immunostimulating substances in the course of the present invention. Although such additional adjuvants may be also added to the present vaccine, they cannot substitute the immunostimulating substance selected according to the present invention.

HGH is specifically preferred for the present invention as immunostimulating substance. Several isoforms are known for this protein, recombinant forms of such isoforms being specifically preferred for the present invention. Preferably, HGH is administered in a stabilized composition according to the present invention, especially with stabilizers such as glycine, tensides, mannitol or polyoxyethylene-polyoxypropylene block copolymers, and buffers, such as sodium phosphate or citrate (WO 89/09614, EP 0 211 601 A, EP 0 587 958 A).

The antigens to be used in the present compositions are not critical. Preferably proteins or peptides derived from a viral or a bacterial pathogen or from fungi or parasites are used as such antigens (including derivatized antigens like glycosylated, lipidated, glycolipidated or hydroxylated antigens. Furthermore, carbohydrates, lipids or glycolipids may be used as antigens themselves. Preferred pathogens are selected from HIV, HBV, HCV, Influenza virus, Rotavirus, *Staphylococcus aureus, Chlamydia pneumoniae, Mycobacterium tuberculosis, Streptococcus pneumoniae, Bacillus anthracis, Vibrio cholerae, Plasmodium* sp. (*Pl. falciparum, Pl. vivax*, etc.), *Aspergillus* sp. or *Candida albicans*. The derivation process may include the purification of a specific protein from the pathogen, the inactivation of the pathogen as well as the proteolytic or chemical derivatization or stabilization of such a protein. In the same way also tumor antigens (cancer vaccines) or autoimmune antigens may be used in the pharmaceutical composition according to the present invention. With such compositions a tumor vaccination or a treatment for autoimmune diseases may be performed.

Preferably antigens are used which induce an antigen-specific type-1 like tumoral and cell mediated immune response in vivo. CD4- and CD8-epitopes are preferred, especially in connection with vaccines against pathogens and tumors.

Preferred immunostimulating substances include pituitary growth hormones or derivatives thereof, especially proteolytically or recombinantly produced derivatives which exhibit the functional properties of the growth hormone (described e.g. in the U.S. Pat. Nos. 5,854,026 or 5,849,535, 5,424,199 or 5,580,723). It has been shown that such substances are also able to alter the cytokine secretion of T cells, B cells or NK cells, but they may also exert effects on APCs or B cells or NK cells. Their immunostimulating effect was connected in the literature with specific receptors on T cells (s. Levite (1998)).

Other preferred neuroactive compounds are selected from but are not restricted to growth hormones, especially human growth hormone, neurokinin A, vasoactive intestinal peptide, neuropeptide Y, substance P, Thyrotrophin (TSH), Insulin-like growth factor I (IGF-1), prolactin, lactogen, luteinizing hormone, follicle stimulating hormone, dehydroepiandosterone (DHEA), Thymosin, Thymulin, Kentsin, melatonin, semaphorins (s. Levite (1998); Scholzen et al (1998); Aronin et al, Ann. Rev. Physiol. 48 (1986), 537-549; Berczi, Acta Paediatr Suppl. 423 (1997), 70-75; Chappel, J. Acq. Imm. Def. Synd. 20(5) (1999), 423-431; Goldman et al., Ann N.Y. Acad. Sci 419 (1983), 143-155; Spriggs, Curr. Op. Immunol. 11 (1999), 387-391; Delneste et al., J. Immunol. 163 (1999), 3071-3075). Also functional derivatives of such compounds may preferably be used in the present invention. A suitable method for providing such derivatives of naturally occurring substances is disclosed in the U.S. Pat. No. 5,580,723.

It is clear to the man skilled in the art that the terms "neuroactive compounds", "hormones", "compounds having a growth hormone activity" are overlapping and many known substances fell into two or even all three groups. However, these terms are to be understood according to their meaning as generally used in the scientific literature, especially in the literature which deals with immunological research to these substance classes.

The polycationic compound to be used according to the present invention may be any polycationic compound which shows the characteristic effect according to the WO 97/30721. Preferred polycationic compounds are selected from basic polypeptides, organic polycations, basic polyaminoacids or mixtures thereof. These polyaminoacids should have a chain length of at least 4 amino acid residues (see: Tuftsin as described in Goldman et al (1983)). Especially preferred are substances like polylysine, polyarginine and polypeptides containing more than 50% of basic amino acids in a range of more than 8, especially more than 20, amino acid residues or mixtures thereof.

These polycationic compounds may be produced chemically or recombinantly or may be derived from natural sources. Preferred polycationic compounds derived from natural sources include HIV-REV or HIV-TAT derived cationic peptides, antennapedia peptides, chitosan (or other derivatives of chitin) and other peptides derived from these peptides or proteins by biochemical or recombinant production.

It was very surprising that with the pharmaceutical composition according to the present invention the immunostimulating effect was significantly higher than it could be expected from the addition of the effects of each single component or even the addition of the effects of the polycation with the antigen and the immunostimulating substance selected according to the present invention with the antigen. Moreover, it turned out that the effect of the selected immunostimulating substances alone is not very high when an antigen is directly applied with this substance. This is true in particular if the compounds are not repeatedly administered.

According to another aspect the present invention also relates to vaccines which comprise a composition according to the present invention.

Moreover, the present invention is also drawn to the use of the composition according to the present invention for manufacturing a vaccine.

The relative amounts of the ingredients of the present composition are highly dependent on the necessities of the individual composition, e.g. the polycationic polymer to be used. In the case of poly-L-arginine and poly-L-lysine, preferred amounts of antigen/immunostimulating compound/polycation lie in the range of 1-10000 µg antigen per vaccination, 0.001 to 1000 units of immunostimulating compound per dose, especially in the case of hormones, such as HGH, and 0.1 to 1000 µg polycation.

The present compositions may be applied to a patient, e.g. a vaccination candidate, in sufficient amounts e.g. by weekly, bi-weekly or monthly intervals. Patients to be treated with the present compositions may also be vaccinated repeatedly or only once. A preferred use of the present invention is the active immunisation, especially of humans or animals without protection against the specific antigen.

The route of application for the present composition is not critical, e.g. subcutaneous, intramuscular, intradermal or transdermal injection is suitable as well as oral uptake.

It is also possible to apply the present composition separately e.g. by injecting the immunostimulating substance separately from the antigen/polycation composition. The present invention is therefore also directed to a kit comprising a composition containing the antigen and the polycationic polymer as one component and a composition containing the stimulating or chemotactic substance as a second component.

The components may be applied at the same site or time, however, an application at different sites or at a different time or for a different time period is also possible. It is also possible to vary the systemic or local applications of the composition or the components, respectively.

In a further aspect the present application relates to a vaccine against HCV infections comprising a polycationic polymer, an immunostimulating substance and an HCV antigen being selected from the group consisting of Core 23-44 (KFPGGGQIVGGVYLLPRRGPRL) (SEQ ID NO:1), CORE 131-150 (ADLMGYIPLVGAPLGGAARA) (SEQ ID NO:2), CORE 132-140 (DLMGYIPAV) (SEQ ID NO:3), NS3 1073-1081 (CINGVCWTV) (SEQ ID NO:4), NS3 1207-1226 (SPVFTDNSSPPAVPQSFQVA) (SEQ ID NO:5), NS3 1248-1261 (GYKVLVLNPSVAAT) (SEQ ID NO:6), NS3 1585-1604 (YLVAYQATVCARAQAPPPSW) (SEQ ID NO:7), NS4 1655-1675 (VVTSTWVLVGGVLAALAAYCL) (SEQ ID NO:8), NS4 1765-1784 (MWNFISGIQYLAGLSTLPGN) (SEQ ID NO:9), NS4 1909-1929 (GEGAVQWMNRLIAFASRGNHV) (SEQ ID NO:10), NS4 1785-1804 (PAIASLMAFTAAVTSPLTTG) (SEQ ID NO:11), NS4 1787-1799 (IASLMAFTAAVTS) (SEQ ID NO:12), NS4 1805-1824 (QTLLFNILGGWVAAQLAAPG) (SEQ ID NO:13) NS4 1809-1821 (FNILGGWVAAQLA) (SEQ ID NO:14), and CD4- and CD8-epitopes with at least 6, preferably 8 to 10, amino acid long fragments of said antigens or strain variants of those antigens. Numbering of the amino acid residues relates to standard HCV nomenclature. The CD8 epitopes are especially selected from Core 31-40, Core 35-44, Core 132-140, NS3 1585-1593, NS3 1585-1594, NS4 1666-1675, NS4 1769-1777, NS4 1773-1783, NS4 1787-

1795, NS4 1789-1797, NS4 1789-1798, NS4 1807-1816, NS4 1809-1817 and NS4 1811-1820.

These HCV epitopes have been shown to be surprisingly effective in vaccines containing polycationic peptides, especially polyarginine.

These carefully selected peptides are conserved in the dominant genotypes of HCV which are—especially in combination with polyarginine—highly immunogenic and therefore surprisingly effective as vaccines. Although a vast variety of peptides and epitopes have been described as potential vaccine candidates for HCV it turned out that only the above mentioned epitopes together with polycationic substances (especially polyamino acids) such as polyarginine could provide the desired results. Therefore, the present invention also relates to a vaccine comprising the selected HCV antigens together with the polyamino acid adjuvants, especially polyarginine, and optionally the immunogenic compounds according to the present invention.

Details of the present invention are described by the following examples and the figures but the invention is of course not limited thereto.

DETAILED DESCRIPTION OF THE ILLUSTRATIVE EMBODIMENTS

EXAMPLES

Example 1

Induction of Antigen Specific T Cells is Greatly Enhanced by Coinjection of Combination of Poly-L-arginine and Human Growth Hormone

| | |
|---|---|
| Mice | C57BL/6 (Harlan/Olac) |
| Peptide | VYDFFVWL (SEQ ID NO: 15) derived from mouse tyrosinase related protein-2. Restricted to H-2Kb (Bloom et al., 1997). Dose: 100 µg/mouse. |
| Control peptide | SIINFEKL (SEQ ID NO: 16) derived from ovalbumin Restricted to H-2Kb (Carbone and Bevan, 1989). |
| Poly-L-arginine 60 (pR60) | poly-L-arginine with an average degree of polymerization of 60 arginine residues; SIGMA chemicals Dose: 100 µg/mouse |
| Human Growth Hormone (HGH) | 0.02 IU/injection SAIZEN, Laboratoires Serono) |

Peptides were synthesized by standard solid phase F-moc synthesis, HPLC purified and analysed by mass spectroscopy for purity.

Figure 1:
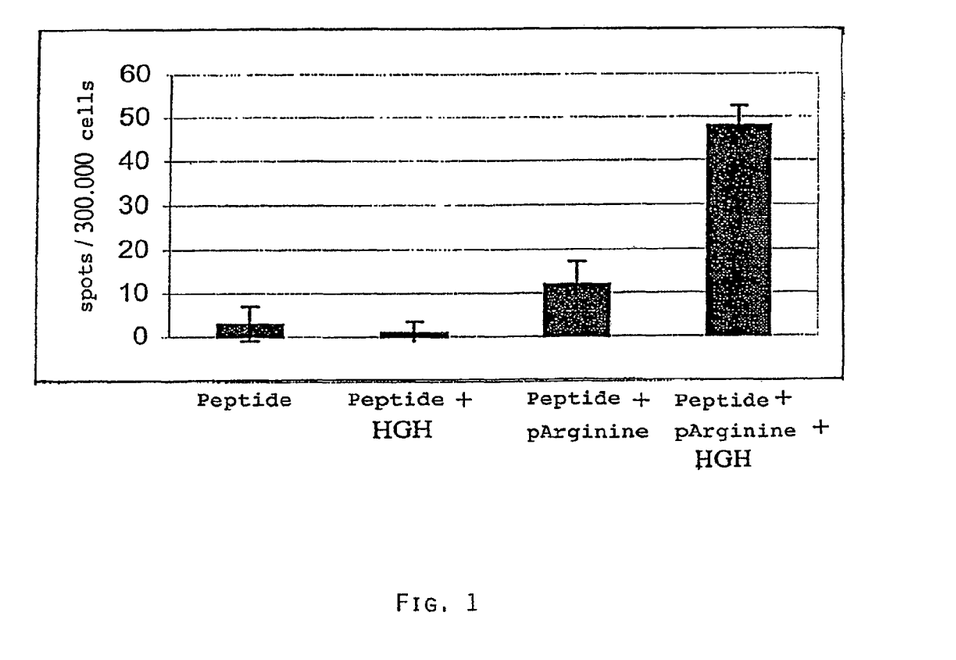
FIG. 1 shows the synergistic action of poly-L-arginine and human growth hormone in the induction of antigen specific T cells.

Experimental Groups (5 Mice Each)
1) TRP-2 peptide
2) TRP-2 peptide+HGH
3) TRP-2 peptide+pR 60
4) TRP-2 peptide+pR 60+HGH On day 0 mice were injected subcutaneously with a total volume of 100 µl containing the above mentioned compounds. Animals were sacrificed 10 days after injection of the vaccine and mesenteric and inguinal lymph nodes harvested. Results are illustrated in FIG. 1.

Lymphocytes were prepared from lymph nodes as follows: cells were passed through a 70 µm sieve and washed twice with DMEM medium (GIBCO BRL) containing 2.5% fetal calf serum (FCS; SIGMA chemicals). Cells were adjusted to $10^7$ cells/ml in complete medium (DMEM+10% FCS). IFN-γ-ELISPOT assays were carried out in triplicate as described (Miyahira et al., 1995). This method is a widely used procedure allowing the quantification of antigen-specific T cells. Lymphocytes were restimulated with TRP-2 peptide or with an ovalbumin-derived peptide (SIINFEKL) with the same MHC restriction serving as negative control.

Spots representing single T cells specific for the peptide used for re-stimulation (and immunization) were counted. The number of background spots observed with cells incubated without peptide(s) was subtracted from all samples. There were no spots detected when the ovalbumine derived peptide was used. The number of spots resulting from the restimulation with the TRP-2 derived peptide are shown below for each group of mice.

Example 2

Preferred Antigens to be Used for Providing a Vaccine Composition According to the Present Invention 1. HCV: antigens according to table 1 and the antigens disclosed in Lamonaca et al., Hepatology 30(4) (1999), 1088-1098.

Hepatitis C Peptides

TABLE 1

| CD4 epitopes | Sequence | References | CD8 epitopes | Sequences | References |
|---|---|---|---|---|---|
| Core 23-44 | KFPGGGQIVGGVYLLPRRGPRL (SEQ ID NO: 1) | (Hoffmann et al., 1995) | Core 132-140 | DLMGYIPAV (SEQ ID NO: 3) | (Sarobe et al., 1998) |
| E2/NS1 | — | — | E2/NS1 723-731 | FLLLADARV (SEQ ID NO: 17) | (Wentworth et al., 1996) |
| NS3 1248-1261 | GYKVLVLNPSVAAT (SEQ ID NO: 6) | (Diepolder et al., 1997) | NS3 1073-1081 | CINGVCWTV (SEQ ID NO: 4) | (He et al., 1999; Rehermann et al., 1996) |
| Core 131-150 | ADLMGYIPLVGAPLGGAARA (SEQ ID NO: 2) | (Hoffmann et al., 1995) | | | |

Notes:
Core 23-44 contains two CD8 epitopes: core 31-40 (VGGVYLLPRR) (SEQ ID NO: 18) and core 35-44 (YLLPRRGPRL) (SEQ ID NO: 19) (Battegay et al., 1995; Rehermann et al., 1996)
Core 131-150 contains the CD8 epitope core 132-140 (DLMGYIPLV) (SEQ ID NO: 20) (Wentworth et al., 1996)

2. HIV: antigens according to table 2

TABLE 2

| Peptide | Sequence |
|---|---|
| Gag 77-85 | SLYNTVATL (SEQ ID NO: 21) |
| Envelope 77-85 | DPNPQEVVL (SEQ ID NO: 22) |
| POL 476-484 | ILKEPVHGV (SEQ ID NO. 23) |

3. Epstein-Barr virus: the antigens according to table 1 of Rickinson et al Ann. Rev. Immunol. 15 (1997), 405-431.

Example 3

Co-Injection of Substance P and pArg

Substance P was tested as a further example for a neuroactive peptide (Marx, Science 205 (1979), 886). Substance P (RPKPQQFFGLM-NH$_2$; SP) (SEQ ID NO:24) was synthesized and purified according to standard procedures. Experiments were conducted as in Example 1 with the exception that spleens instead of lymph nodes were used.

Splenocytes were prepared from spleens as follows: cells were passed through a 70 μm sieve and washed once with DMEM medium (GIBCO BRL). Red blood cells were lysed with "red blood cells lysis buffer" (Sigma) for 1 minute and washed twice with DMEM medium (GIBCO BRL). Cells were adjusted to 3*10$^6$ cells/ml in complete medium (DEMEM+5% FCS). IFN-γ-ELISPOT was carried out as described (Miyahira et al., 1995).

Experimental Groups (2 Mice Each)
1) TRP-2 peptide
2) TRP-2 peptide+pR 60
3) TRP-2 peptide+pR 60+substance P Per injection 10 nmoles SP have been administered to mice.

Figure 2:
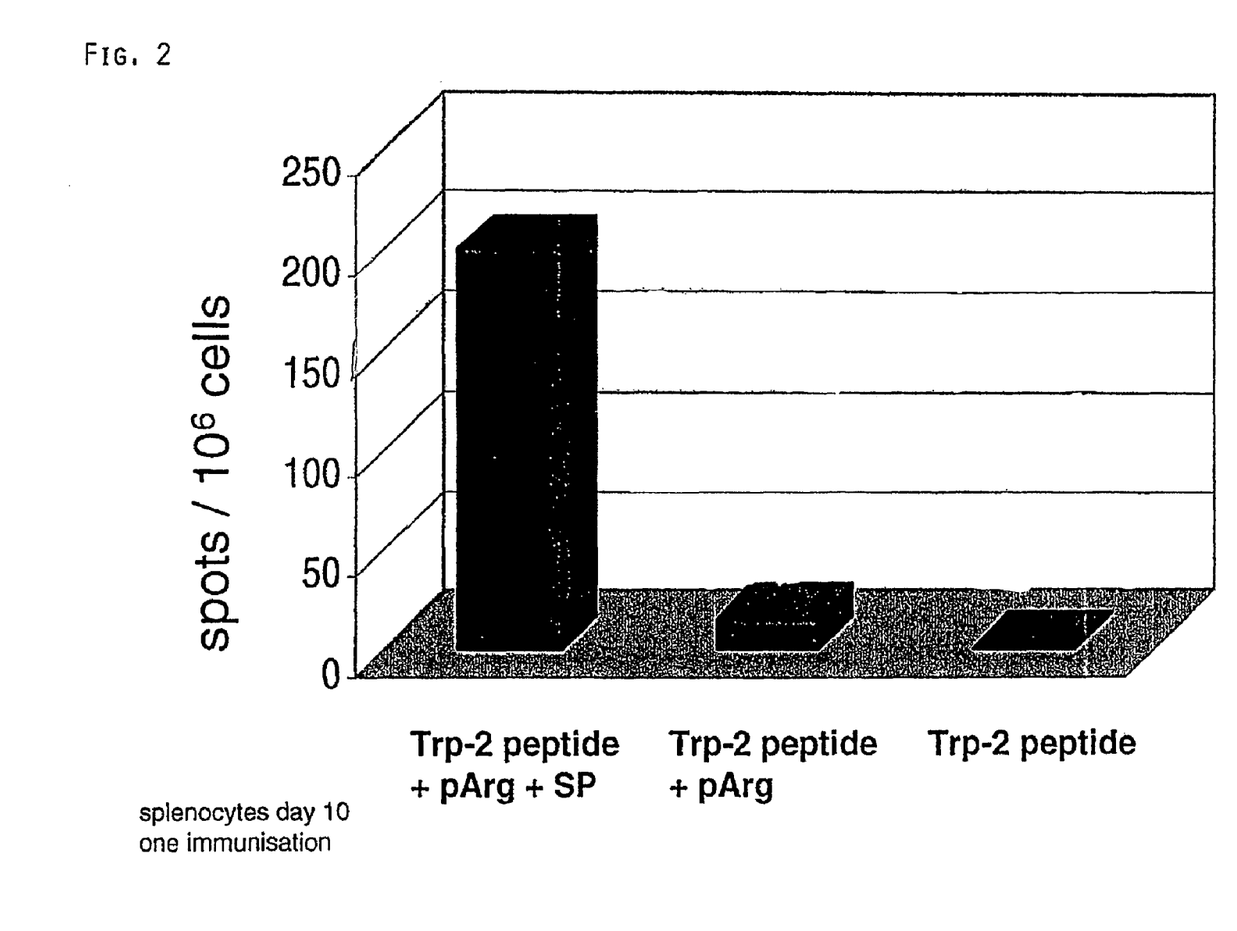
FIG. 2 shows the synergistic action of poly-L-arginine and substance P in the induction of antigen specific T cells.

The results are depicted in FIG. 2. It is demonstrated with the present example that co-injection of SP and poly-L-arginine results in greatly enhanced generation of T cells in an IFN-γ-ELISPOT essay.

The invention claimed is:

1. An immunogenic composition comprising an isolated HCV antigen consisting of SEQ ID NO: 1 and a polycationic compound.

2. The composition of claim 1, wherein the polycationic compound is a basic polypeptide, an organic polycation, a basic polyaminoacid or a mixture of such compounds.

3. The composition of claim 1, wherein the polycationic compound comprises polyarginine, polylysine, a polypeptide of more than 8 amino acids containing more than 50% basic amino acid residues, or a mixture of such compounds.

4. The composition of claim 1, wherein the polycationic compound comprises a polypeptide of more than 20 amino acids containing more than 50% basic amino acid residues.

5. The composition of claim 1, wherein the polycationic compound is polyarginine.

6. The composition of claim 1, further comprising an additional immunostimulating compound.

7. The composition of claim 6, wherein the additional immunostimulating compound is selected from the group consisting of growth hormones, human growth hormones, neurokinin A, vasoactive intestinal peptide, neuropeptide Y, substance P, thyrotrophin (TSH), insulin-like growth factor I (IGF-1), prolactin, lactogen, luteinizing hormone, follicle stimulating hormone, dehydroepiandrosterone (DHEA), thymosin, thymulin, kentsin, melatonin, semaphorins, and a mixture of such compounds.

8. The composition of claim 1, further comprising a stabilizer.

9. The composition of claim 1, wherein the composition is in liquid form.

10. A method of inducing an immune response against HCV in a subject comprising administering to the subject the composition of claim 1.

11. The method of claim 10, wherein the composition is administered via a route selected from the group consisting of subcutaneous, intramuscular, intradermal, transdermal injection, and oral uptake.

12. The method of claim 10, wherein the composition is administered to a subject at weekly, bi-weekly or monthly intervals.

13. A method of inducing an immune response against HCV in a subject comprising administering to the subject the composition of claim 1 and an additional immunostimulating compound, wherein the additional immunostimulating compound is administered separately from the composition of claim 1.

14. A kit comprising:

a component comprising the composition of claim 1; and a component comprising an additional immunostimulating compound.

* * * * *